US006939923B2

(12) United States Patent
Bohling et al.

(10) Patent No.: US 6,939,923 B2
(45) Date of Patent: Sep. 6, 2005

(54) RESIN FOR SOLID PHASE SYNTHESIS

(75) Inventors: James Charles Bohling, Lansdale, PA (US); Marlin Kenneth Kinzey, Philadelphia, PA (US); John Joseph Maikner, Zionsville, PA (US); William Joseph Zabrodski, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 10/636,186

(22) Filed: Aug. 7, 2003

(65) Prior Publication Data

US 2004/0034173 A1 Feb. 19, 2004

Related U.S. Application Data

(60) Provisional application No. 60/404,044, filed on Aug. 16, 2002.

(51) Int. Cl.$^7$ .......................... C08G 63/91; C08F 112/08
(52) U.S. Cl. .......................... 525/333.3; 525/64; 525/69; 528/396; 528/492
(58) Field of Search ................................ 525/64, 333.3, 525/69, 61, 332.3; 528/396, 492

(56) References Cited

U.S. PATENT DOCUMENTS

| | | | |
|---|---|---|---|
| 3,562,203 A | 2/1971 | Grunin et al. | |
| 3,873,668 A | 3/1975 | Russell | |
| 4,031,038 A | 6/1977 | Grinstead et al. | |
| 4,038,469 A | * 7/1977 | Walker et al. | 525/327.1 |
| 4,187,382 A | 2/1980 | Cowherd, III et al. | |
| 4,486,313 A | 12/1984 | Meitzner et al. | |
| 4,978,724 A | 12/1990 | Clark | |
| 5,182,026 A | 1/1993 | Pike | |
| 5,330,687 A | * 7/1994 | Rieke | 260/665 R |
| 5,939,494 A | * 8/1999 | Wehmeyer et al. | 525/333.5 |
| 6,214,618 B1 | 4/2001 | Hillegas et al. | |
| 6,387,974 B1 | 5/2002 | Deissler et al. | |
| 6,410,643 B1 | 6/2002 | Swanson | |

FOREIGN PATENT DOCUMENTS

WO     WO0206384 A1     1/2002

OTHER PUBLICATIONS

Rana et al., Influence of Resin Cross–linking on Solid–Phase Chemistry, *J. Comb. Chem.*, 3, pp. 9–15 (2001).
Vaino et al., Solid–Phase Organic Synthesis: A Critical Understanding of the Resin, *J. Comb. Chem.*, 2, pp. 579–596, (2000).
Borhan et al., Suspension Copolymerization as a Route to Trityl–Functionalized Polystyrene Polymers, *J. Org. Chem.*, 60, pp. 7375–7376, (1995).
Groth et al., Diffusion Of Reagents In Macrobeads, *J. Comb. Chem.*, pp. 3, 461–468, (2001).

* cited by examiner

*Primary Examiner*—James J. Seidleck
*Assistant Examiner*—Irina S. Zemel
(74) *Attorney, Agent, or Firm*—Kenneth Crimaldi

(57) ABSTRACT

A method for functionalizing a crosslinked polymer bead. The method comprises the steps of: (a) swelling the bead in a first solvent or solvent mixture to a volume from 200% to 310% of its volume when dry; and (b) contacting the bead with a functionalizing reagent in a second solvent or solvent mixture capable of swelling the bead to a volume from 200% to 310% of its volume when dry.

3 Claims, No Drawings

RESIN FOR SOLID PHASE SYNTHESIS

CROSS REFERENCE TO RELATED PATENT APPLICATIONS

This is a non-provisional application of prior pending U.S. provisional application Ser. No. 60/404,044 filed Aug. 16, 2002.

This invention relates to functionalized polymeric resins useful as supports in solid phase synthesis. The present invention also relates to methods to prepare such resins.

Lightly crosslinked resins have found significant utility as solid supports for solid phase organic synthesis processes, such as for the production of polypeptides from amino acids. Such resins typically are less than three percent crosslinked. Accessibility of functional groups on the resin is of great importance in solid phase synthesis, as it controls yields, kinetics, raw material use, and product purity. Lowering the resin crosslinking can increase the ability of the resin to swell, which increases accessibility of functional groups. See, for example, S. Rana et al., "Influence of Resin Cross-Linking on Solid-Phase Chemistry," *J. Comb. Chem.*, 2001, 3, 9–15. However, this leads to a softer resin, which is more difficult to process, and to greater volume requirements in the resin bed.

The problem addressed by this invention is to develop a crosslinked polymeric support for solid phase synthesis having accessible functional groups without a high degree of swelling.

STATEMENT OF INVENTION

The present invention provides a method for functionalizing a crosslinked polymer bead; said method comprising steps of: (a) swelling the bead in a first solvent or solvent mixture to a volume from 200% to 310% of its volume when dry; and (b) contacting the bead with a functionalizing reagent in a second solvent or solvent mixture capable of swelling the bead to a volume from 200% to 310% of its volume when dry.

The present invention further provides a method for functionalizing a crosslinked polymer bead by contacting the bead at 100% to 200% of its volume when dry with a functionalizing reagent in a solvent or solvent mixture capable of swelling the bead to a volume from 200% to 400% of its volume when dry.

DETAILED DESCRIPTION

Percentages are weight percentages, unless specified otherwise. As used herein the term "(meth)acrylic" refers to acrylic or methacrylic. The term "vinyl monomer" refers to a monomer suitable for addition polymerization and containing a single polymerizable carbon-carbon double bond. The term "styrene polymer" indicates a copolymer polymerized from a vinyl monomer or mixture of vinyl monomers containing at least 50 weight percent, based on the total monomer weight, of styrene monomer, along with at least one crosslinker. Preferably a styrene polymer is made from a mixture of monomers that is at least 75% styrene, more preferably at least 90% styrene, and most preferably from a mixture of monomers that consists essentially of styrene and at least one vinylaromatic crosslinker. The polymeric bead used as a starting material in this invention contains monomer residues from at least one monomer having one copolymerizable carbon-carbon double bond and at least one crosslinker. The monomer residues derived from the crosslinker are from 0.5 mole percent to 1.5 mole percent based on the total of all monomer residues. Preferably the amount of crosslinker is from 0.7 to 1.3 mole percent, more preferably from 0.7 to 1.2 mole percent, and most preferably from 0.8 to 1.2 mole percent.

A polymeric bead used as a starting material in the present invention preferably is a spherical copolymer bead having a particle diameter no greater than 200 microns ($\mu$m), preferably no greater than 170 $\mu$m, more preferably no greater than 150 $\mu$m, more preferably no greater than 125 $\mu$m, and most preferably no greater than 100 $\mu$m. Preferably, the bead has no void spaces having a diameter greater than 3 $\mu$m, more preferably no void spaces having a diameter greater than 2 $\mu$m, and most preferably no void spaces having a diameter greater than 1 $\mu$m. Typically, void spaces are readily apparent upon surface examination of the bead by a technique such as light microscopy.

The polymeric bead used as a starting material in the present invention preferably is produced by a suspension polymerization. A typical bead preparation, for example, may include preparation of a continuous aqueous phase solution containing typical suspension aids, for example, dispersants, protective colloids and buffers. Preferably, to aid in production of relatively small beads, a surfactant is included in the aqueous solution, preferably a sodium alkyl sulfate surfactant, and vigorous agitation is maintained during the polymerization process. The aqueous solution is combined with a monomer mixture containing at least one vinyl monomer, at least one crosslinker and at least one free-radical initiator. Preferably, the total initiator level is from 0.25 mole percent to 2 mole %, based on the total monomer charge, preferably from 0.4 mole percent to 1.5 mole percent, more preferably from 0.4 mole percent to 1 mole percent, and most preferably from 0.5 mole percent to 0.8 mole percent. The mixture of monomers is then polymerized at elevated temperature. Preferably, the polymerization is continued for a time sufficient to reduce the unreacted vinyl monomer content to less than 1% of the starting amount. The resulting bead is then isolated by conventional means, such as dewatering, washing with an aprotic organic solvent, and drying.

Crosslinkers are monomers having 2 or more copolymerizable carbon-carbon double bonds per molecule, such as: divinylbenzene, divinyltoluene, divinylxylene, trivinylbenzene, trivinylcyclohexane, divinylnaphthalene, trivinylnaphthalene, diethyleneglycol divinylether, ethyleneglycol dimethacrylate, polyethyleneglycol dimethacrylate triethyleneglycol dimethacrylate, trimethylolpropane trimethacrylate, allyl methacrylate, 1,5-hexadiene, 1,7-octadiene or 1,4-bis(4-vinylphenoxy)butane; it is understood that any of the various positional isomers of each of the aforementioned crosslinkers is suitable. Preferred crosslinkers are divinylbenzene, divinyltoluene, trivinylbenzene or 1,4-bis(4-vinylphenoxy)butane. The most preferred crosslinker is divinylbenzene.

Suitable monounsaturated vinylaromatic monomers that may be used in the preparation of the bead used as a starting material in the present invention include, for example, styrene, $\alpha$-methylstyrene, ($C_1$–$C_4$)alkyl-substituted styrenes and vinylnaphthalene; preferably one or more monounsaturated vinylaromatic monomer is selected from the group consisting of styrene and ($C_1$–$C_4$)alkyl-substituted styrenes. Included among the suitable ($C_1$–$C_4$)alkyl-substituted styrenes are, for example, ethylvinylbenzenes, vinyltoluenes, diethylstyrenes, ethylmethylstyrenes, dimethylstyrenes and isomers of vinylbenzyl chloride; it is understood that any of the various positional isomers of each of the aforementioned vinylaromatic monomers is suitable.

Optionally, non-aromatic vinyl monomers, such as aliphatic unsaturated monomers, for example, acrylonitrile, glycidyl methacrylate, (meth)acrylic acids and amides or $C_1$–$C_6$ alkyl esters of (meth)acrylic acids may also be used in addition to the vinylaromatic monomer. When used, the non-aromatic vinyl monomers typically comprise as polymerized units, from zero to 20%, preferably from zero to 10%, and more preferably from zero to 5% of the copolymer, based on the total monomer weight used to form the copolymer.

Preferred vinyl monomers are the vinylaromatic monomers; more preferably styrene, isomers of vinylbenzyl chloride, and α-methylstyrene. The most preferred vinyl monomer is styrene.

Polymerization initiators useful in the present invention include monomer-soluble initiators such as peroxides, hydroperoxides, peroxyesters and related initiators; for example benzoyl peroxide, tert-butyl hydroperoxide, cumene peroxide, tetralin peroxide, acetyl peroxide, caproyl peroxide, tert-butyl peroctoate (also known as tert-butylperoxy-2-ethylhexanoate), tert-amyl peroctoate, tert-butyl perbenzoate, tert-butyl diperphthalate, dicyclohexyl peroxydicarbonate, di(4-tert-butylcyclohexyl) peroxydicarbonate and methyl ethyl ketone peroxide. Also useful are azo initiators such as azodiisobutyronitrile, azodiisobutyramide, 2,2'-azo-bis(2,4-dimethylvaleronitrile), azo-bis(α-methyl-butyronitrile) and dimethyl-, diethyl- or dibutyl azo-bis(methylvalerate). Preferred peroxide initiators are diacyl peroxides, such as benzoyl peroxide, and peroxyesters, such as tert-butyl peroctoate and tert-butyl perbenzoate.

Dispersants and suspending agents useful in the present invention are nonionic surfactants having a hydroxyalkyl-cellulose backbone, a hydrophobic alkyl side chain containing from 1 to 24 carbon atoms, and an average of from 1 to 8, preferably from 1 to 5, ethylene oxide groups substituting each repeating unit of the hydroxyalkyl-cellulose backbone, the alkyl side chains being present at a level of 0.1 to 10 alkyl groups per 100 repeating units in the hydroxyalkyl-cellulose backbone. The alkyl group in the hydroxyalkyl-cellulose may contain from 1 to 24 carbons, and may be linear, branched or cyclic. More preferred is a hydroxyethylcellulose containing from 0.1 to 10 ($C_{16}$)alkyl side chains per 100 anhydroglucose units and from about 2.5 to 4 ethylene oxide groups substituting each anhydroglucose unit. Typical use levels of dispersants are from about 0.01 to about 4%, based upon the total aqueous-phase weight.

Optionally, the preparation of the beads may include an enzyme treatment to cleanse the polymer surface of residues of dispersants and suspending agents used during the polymerization. The enzyme treatment typically involves contacting the polymeric phase with the enzymatic material (selected from one or more of cellulose-decomposing enzyme and proteolytic enzyme) during polymerization, following polymerization or after isolation of the polymer. Japanese Patent Applications No. 61-141704 and No. 57-98504 may be consulted for further general and specific details on the use of enzymes during the preparation of polymer resins. Suitable enzymes include, for example, cellulose-decomposing enzymes, such as β-1,4-glucan-4-glucano-hydrase, β-1,4-glucan-4-glucanhydrolase, β-1,4-glucan-4-glucohydrase and β-1,4-glucan-4-cellobiohydrase, for cellulose-based dispersant systems; and proteolytic enzymes, such as urokinase, elastase and enterokinase, for gelatin-based dispersant systems. Typically, the amount of enzyme used relative to the polymer is from 2 to 35%, preferably from 5 to 25% and more preferably from 10 to 20%, based on total weight of polymer.

In the method of the present invention, the swelling of the crosslinked polymeric beads is controlled so that the bead is partially swelled during functionalization. Without wishing to be bound by theory, the effect of functionalizing a partially swollen bead is to limit the location of the attached functional groups to a region relatively close to the surface of the bead. Preferably, when the functionalization occurs, the bead is swollen to at least 200% of its volume when dry, more preferably at least 210%, more preferably at least 220%, more preferably at least 230%, and most preferably at least 240%. Preferably, the bead is swollen to no more than 310% of its volume when dry, more preferably no more than 300%, more preferably no more than 290%, and most preferably no more than 280%. There are different means for accomplishing the desired degree of swelling during functionalization.

In one embodiment of the invention, a bead which is not pre-swollen (i.e., at 100% of its volume when dry), or which is pre-swollen to no more than 200% of its volume when dry, is contacted with a functionalizing reagent in a solvent or solvent mixture capable of swelling the bead to at least 200% of its volume when dry, more preferably at least 210%, more preferably at least 220%, more preferably at least 230%, and most preferably at least 240%. Preferably, the solvent or solvent mixture is capable of swelling the bead to no more than 400% of its volume when dry, more preferably no more than 370%, more preferably no more than 340%, and most preferably no more than 320%. Preferably, the bead is pre-swollen to no more than 150%, more preferably no more than 100%, more preferably no more than 80%, more preferably no more than 60%, and most preferably no more than 40%. In one embodiment, the bead is used in its dry state without pre-swelling.

In another embodiment of the invention, the bead is pre-swollen in a solvent or solvent mixture which swells the bead to at least 200% of its volume when dry, more preferably at least 210%, more preferably at least 220%, more preferably at least 230%, and most preferably at least 240%. Preferably, the bead is swollen to no more than 310% of its volume when dry, more preferably no more than 300%, more preferably no more than 290%, and most preferably no more than 280%. After pre-swelling, the bead is contacted with a functionalizing reagent in a solvent or solvent mixture capable of swelling the bead within the aforementioned limits. Most preferably, the solvents or solvent mixtures used for pre-swelling and functionalization are the same.

A functionalizing reagent is one which covalently attaches a functional group to the polymer comprising the bead. Further elaboration of the functional group may be necessary to maximize the utility of the bead as a support for solid phase synthesis. However, the initial attachment of the functional group determines the region of the bead which is functionalized and thus tends to control the ability of the bead to react with substrates for solid phase synthesis and to allow recovery of the synthetic product. For styrene polymers, the functionalization typically is a Friedel-Crafts substitution on the aromatic ring, preferably an acylation, bromination, or halomethylation. Subsequent elaboration of the initial functional group typically is done. For example, acylation by aroyl halides often is followed by addition of an aryl lithium to the carbonyl group of the product to produce a triaryl carbinol functional group, which then is halogenated. Bromination typically is followed by treatment with an alkyl lithium reagent and reaction of the aryl lithium product with a variety of reagents to produce different functional groups. Halomethyl groups also may react with a variety of reagents to produce different functional groups.

Solvents capable of partially swelling the bead include, for example, $C_1$–$C_6$ nitroalkanes, and mixtures of relatively non-swelling solvents such as alkanes with nitrobenzene or chlorinated hydrocarbons. For functionalization using Friedel-Crafts chemistry, $C_3$–$C_6$ nitroalkanes, and mixtures of relatively non-swelling solvents such as alkanes with nitrobenzene are preferred.

EXAMPLES

Comparative Example 1

Internal and Surface Functionalization of Pre-Swelled Crosslinked Polystyrene Beads A 1L round bottom flask fitted with an overhead stirrer, $N_2$ inlet fitted with a pressure relief upstream, and a thermocouple was purged with a light positive pressure of nitrogen (sweep against open stopper while making additions). Nitrobenzene (400 mL) was charged and held at room temperature. A polystyrene resin (40 g, 0.379 mol) was charged against the nitrogen sweep and stirred for ½ hour. Chlorobenzoyl chloride (24.89 g, 0.142 mol) was charged to the flask and stirred for 15 minutes. Inside a glove bag filled with nitrogen, aluminum chloride (18.96 g, 0.142 mol) was weighed into a sealed bottle, which then was charged into the reaction flask against the nitrogen sweep. The contents of the flask were heated to 30° C. and held for 4 hours. The reaction mixture was poured into a buchner filter funnel, and the reaction flask washed with a small amount of nitrobenzene to complete transfer. The filter was drained to resin level, and nitrobenzene (280 mL, 1 bed volume) was added, and the filter drained again. Tetrahydrofuran ("THF") (2 bed volumes) was added on top of resin bed, which was allowed to drain. The color was removed as the THF replaced the nitrobenzene. One bed volume of 4:1 THF:$H_2O$ was added and the resin was re-suspended, then the filter was drained to the resin level and one bed volume of THF was added on top of the resin. The filter was allowed to drain to the resin level. One bed volume of THF was added and the resin was re-suspended, then the filter was drained to the resin level and one bed volume of THF was added on top of the resin. The filter was allowed to drain to the resin level. One bed volume of methanol was added on top of resin. The filter was allowed to drain to the resin level. One bed volume of methanol was added and the resin was re-suspended, then the filter was drained to the resin level and one bed volume of methanol was added on top of the resin. The filter was allowed to drain to the resin level. Minimal vacuum was applied to remove excess solvent. The resin was dried in a 35° C. vacuum oven to a constant weight.

Example 1

Surface Functionalization of a Crosslinked Polystyrene Bead by Functionalization of Unswelled Beads A 1L round bottom flask fitted with an overhead stirrer, $N_2$ inlet fitted with a pressure relief upstream, and a thermocouple was purged with a light positive pressure of nitrogen (sweep against open stopper while making additions). Nitrobenzene (400 mL) was charged and held at room temperature. Inside a glove bag filled with nitrogen, aluminum chloride (18.96 g, 0.142 mol) was weighed into a sealed bottle, which then was charged into the reaction flask against the nitrogen sweep. After the aluminum chloride was dissolved (ca. 5 minutes), chlorobenzoyl chloride (24.89 g, 0.142 mol) was charged to the flask and stirred for 5 minutes. A polystyrene resin (40 g, 0.379 mol) was charged against the nitrogen sweep and stirred for ½ hour. The contents of the flask were heated to 30° C. and held for 4 hours. The reaction mixture was poured into a buchner filter funnel, and the reaction flask washed with a small amount of nitrobenzene to complete transfer. The filter was drained to resin level, and nitrobenzene (280 mL, 1 bed volume) was added, and the filter drained again. Tetrahydrofuran ("THF") (2 bed volumes) was added on top of resin bed, which was allowed to drain. The color was removed as the THF replaced the nitrobenzene. One bed volume of 4:1 THF:$H_2O$ was added and the resin was re-suspended, then the filter was drained to the resin level and one bed volume of THF was added on top of the resin. The filter was allowed to drain to the resin level. One bed volume of THF was added and the resin was re-suspended, then the filter was drained to the resin level and one bed volume of THF was added on top of the resin. The filter was allowed to drain to the resin level. One bed volume of methanol was added on top of the resin. The filter was allowed to drain to the resin level. One bed volume of methanol was added and the resin was re-suspended, then the filter was drained to the resin level and one bed volume of methanol was added on top of the resin. The filter was allowed to drain to the resin level. Minimal vacuum was applied to remove excess solvent. The resin was dried in a 35° C. vacuum oven to a constant weight.

Example 2

Surface Functionalization of Crosslinked Polystyrene Beads by Selection of Functionalization Solvent A 1L round bottom flask fitted with an overhead stirrer, $N_2$ inlet fitted with a pressure relief upstream, and a thermocouple is purged with a light positive pressure of nitrogen (sweep against open stopper while making additions). Nitroethane (400 mL) is charged and held at room temperature. A polystyrene resin (40 g, 0.379 mol) is charged against the nitrogen sweep and stirred for ½ hour. Chlorobenzoyl chloride (24.89 g, 0.142 mol) is charged to the flask and stirred for 15 minutes. Inside a glove bag filled with nitrogen, aluminum chloride (18.96 g, 0.142 mol) is weighed into a sealed bottle, which then is charged into the reaction flask against the nitrogen sweep. The contents of the flask are heated to 30° C. and held for 4 hours. The reaction mixture is poured into a buchner filter funnel, and the reaction flask washed with a small amount of nitrobenzene to complete transfer. The filter is drained to resin level, and nitrobenzene (280 mL, 1 bed volume) is added, and the filter drained again. Tetrahydrofuran ("THF") (2 bed volumes) is added on top of the resin bed, which is allowed to drain. The color is removed as the THF replaces the nitrobenzene. One bed volume of 4:1 THF:$H_2O$ is added and the resin is re-suspended, then the filter is drained to the resin level and one bed volume of THF is added on top of the resin. The filter is allowed to drain to the resin level. One bed volume of THF is added and the resin is re-suspended, then the filter is drained to the resin level and one bed volume of THF is added on top of the resin. The filter is allowed to drain to the resin level. One bed volume of methanol is added on top of resin. The filter is allowed to drain to the resin level. One bed volume of methanol is added and the resin is re-suspended, then the filter is drained to the resin level and one bed volume of methanol is added on top of the resin. The filter is allowed to drain to the resin level. Minimal vacuum is applied to remove excess solvent. The resin is dried in a 35° C. vacuum oven to a constant weight.

Example 3

Surface Functionalization of Crosslinked Polystyrene Beads by Use of a Mixed Functionalization Solvent A 1L round bottom flask fitted with an overhead stirrer, $N_2$ inlet fitted with a pressure relief upstream, and a thermocouple is purged with a light positive pressure of nitrogen (sweep against open stopper while making additions). Nitrobenzene (60 mL) and Heptane (440 mL) are charged and held at room temperature. A polystyrene resin (40 g, 0.379 mol) is charged against the nitrogen sweep and stirred for ½ hour. Chlorobenzoyl chloride (24.89 g, 0.142 mol) is charged to the flask and stirred for 15 minutes. Inside a glove bag filled with nitrogen, aluminum chloride (18.96 g, 0.142 mol) is weighed into a sealed bottle, which then is charged into the reaction flask against the nitrogen sweep. The contents of the flask are heated to 30° C. and held for 4 hours. The reaction mixture is poured into a buchner filter funnel, and the reaction flask washed with a small amount of nitrobenzene to complete transfer. The filter is drained to resin level, and nitrobenzene (280 mL, 1 bed volume) is added, and the filter drained again. Tetrahydrofuran ("THF") (2 bed volumes) is added on top of resin bed, which is allowed to drain. The color is removed as the THF replaces the nitrobenzene. One bed volume of 4:1 THF:$H_2O$ is added and the resin is re-suspended, then the filter is drained to the resin level and one bed volume of THF is added on top of the resin. The filter is allowed to drain to the resin level. One bed volume of THF is added and the resin is re-suspended, then the filter is drained to the resin level and one bed volume of THF is added on top of the resin. The filter is allowed to drain to the resin level. One bed volume of methanol is added on top of resin. The filter is allowed to drain to the resin level. One bed volume of methanol is added and the resin is re-suspended, then the filter is drained to the resin level and one bed volume of methanol is added on top of the resin. The filter is allowed to drain to the resin level. Minimal vacuum is applied to remove excess solvent. The resin is dried in a 35° C. vacuum oven to a constant weight.

Example 4

General Procedure for Final Functionalization of Crosslinked Beads

In an oven dried four neck round bottom flask (equipped with a stirrer, a condenser w/nitrogen bubbler, a temperature controller, and a septum) was taken the THF and the dried bead resulting from any of the previous Examples (10:1, volume:weight). The mixture was stirred for 15 minutes, phenyl lithium (1.25 equivalents) was added drop wise over 10 minutes. The temperature was kept <30° C. by an ice/water bath. The reaction mixture was then stirred at ambient temperature for 1 hour. Quenching was accomplished by drop wise addition of 10% aqueous HCl, keeping the reaction temperature below 30° C. The mixture was stirred for 1 hour. The contents are then transferred to a sinter glass funnel and drained to bed height. The resin was then re-suspended in 1 bed volume of 4:1 THF/10% HCl (v/v) and allowed to drain to bed height slowly. The resin was re-suspended with 1 bed volume of 4:1 THF/water and allowed to drain. The bed was then re-suspended and drained 3 times with 1 bed volume of THF, followed by re-suspending/draining 3 times with 1 bed volume of methanol. A final rinse through of the bed is done with 1 bed volume of methanol. Vacuum was applied to remove excess solvent and then the beads were dried in a 35° C. vacuum oven.

In an oven dried four neck round bottom flask (equipped with a stirrer, a temperature controller, a condenser w/nitrogen bubbler, and a stopper) was added the methylene chloride and the dried bead from the previous step (10:1). Added thionyl chloride (5 equivalents) drop-wise followed by N,N-dimethylformamide (5 mole % based on thionyl chloride). The mixture was warmed to reflux (37° C.) for 4 hours. After cooling to ambient temperature, the reaction mixture was transferred to a nitrogen purged sinter glass funnel and drained to bed height. The bed was then re-suspended and drained twice with 1 bed volume of methylene chloride. It was then further washed by re-suspending/draining three times with 1 bed volume of anhydrous hexane. Purged through the bed with nitrogen to remove excess solvent and then placed the beads in a vacuum oven at ambient temperature. The trityl chloride functionalized bead resulting from this preparation is useful, for example, in solid phase peptide synthesis.

Example 5

Swelling of Crosslinked Polystyrene Beads in Various Solvents

Crosslinked polystyrene beads made using 1% and approximately 1.5% divinylbenzene as a crosslinker, and having a volume when dry of 1.65 mL/g were swelled in solvents, with the results presented below in mL/g. Solvent ratios are volume:volume.

| Solvent | 1.5% crosslinker | 1% crosslinker |
| --- | --- | --- |
| nitromethane | 2.5 | N/A |
| nitropropane | 3.7 | 4.05 |
| 1:1, nitropropane:heptane | 3.6 | 4.3 |
| 1:2, nitropropane:heptane | 3.5 | 3.7 |
| 1:3, nitropropane:heptane | 3.3 | 3.55 |
| nitrobenzene | 4.0 | 5.3 |
| 1:1, nitrobenzene:heptane | 4.6 | 5.6 |
| 1:2, nitrobenzene:heptane | 4.5 | 5.05 |
| 1:3, nitrobenzene:heptane | 4.2 | 4.3 |
| methanol | 1.7 | N/A |
| heptane | 1.9 | N/A |

What is claimed is:

1. A method for functionalizing a crosslinked polymer bead by contacting the head with a functionalizing reagent in a solvent or solvent which mixture swells the bead to a volume from 200% to 400% of its volume when dry, wherein the polymer bead is not pre-swollen when contacted with the functionalizing reagent, the bead has from 0.5 mole percent to 1.5 mole percent of monomer residues derived from a crosslinker, and the bead is a styrene polymer.

2. A method for functionalizing a crosslinked polymer bead by contacting the bead with a functionalizing reagent in a solvent or solvent mixture which swells the bead to a volume from 220% to 340% of its volume when dry, wherein the polymer bead is not pre-swollen when contacted with the functionalizing reagent, the bead has from 0.5 mole percent to 1.5 mole percent of monomer residues derived from a crosslinker, and the bead is a styrene polymer.

3. The method of claim 2 in which the solvent or solvent mixture comprises nitrobenzene.

* * * * *

UNITED STATES PATENT AND TRADEMARK OFFICE
CERTIFICATE OF CORRECTION

PATENT NO. : 6,939,923 B2
APPLICATION NO. : 10/636186
DATED : September 6, 2005
INVENTOR(S) : Bohling et al.

Page 1 of 1

It is certified that error appears in the above-identified patent and that said Letters Patent is hereby corrected as shown below:

<u>Column 8,</u>
Line 49, "head" should read -- bead --.
Line 50, "solvent which mixture" should read -- solvent mixture which --.

Signed and Sealed this

Twenty-seventh Day of June, 2006

JON W. DUDAS
*Director of the United States Patent and Trademark Office*